United States Patent [19]

Vaillancourt

[11] Patent Number: 4,723,955

[45] Date of Patent: * Feb. 9, 1988

[54] SUCTION NEEDLE PROVIDING VENT CAPABILITY

[75] Inventor: Vincent L. Vaillancourt, Livingston, N.J.

[73] Assignee: Manresa, Inc., Hillsdale, N.J.

[*] Notice: The portion of the term of this patent subsequent to Sep. 9, 2003 has been disclaimed.

[21] Appl. No.: 869,307

[22] Filed: Jun. 2, 1986

[51] Int. Cl.[4] .............................................. A61B 19/00
[52] U.S. Cl. ...................................... 604/405; 604/45; 604/411
[58] Field of Search ................... 604/44, 45, 164, 165, 604/166, 167, 252, 405, 411, 414, 900; 29/516

[56] References Cited

U.S. PATENT DOCUMENTS

| 2,541,272 | 2/1951 | Murphy | 604/44 |
| 3,094,122 | 6/1963 | Gauthier et al. | 604/164 |
| 4,451,966 | 6/1984 | Lee | 29/516 |
| 4,475,914 | 10/1984 | Portnoff | 604/414 |
| 4,537,593 | 8/1985 | Alchas | 604/411 |
| 4,610,683 | 9/1986 | Vaillancourt | 604/405 |

FOREIGN PATENT DOCUMENTS 0563722 11/1932 Fed. Rep. of Germany ........ 604/44

Primary Examiner—Stephen C. Pellegrino
Assistant Examiner—Ralph Lewis
Attorney, Agent, or Firm—Ralph R. Roberts

[57] ABSTRACT

This suction needle device is used to transfer liquids such as cytotoxic drugs from a stoppered container to a syringe. This device has a sharpened needle which is conventionally attached to a hub. A thin-walled tubular sleeve is mounted on the shank of this needle and is disposed in a telescope fashion around this shank. One end of the sleeve is disposed a short distance from the sharpened end of the needle so that the stopper may be entered by the sharpened needle and sleeve and provides a seal when so penetrated. A crimping tool provides opposed and longitudinally displaced localized crimps to deform the sleeve to the extent that a positive engagement with the shank of the needle is made. The crimps are limited enough to provide positive securing of the sleeve without bending or distorting the interior capacity of the needle to draw fluids into the syringe. The thin-walled sleeve may have an aperture in the side and in flow communication with the air passage between the needle shank and sleeve. Other embodiments show this air passage in flow communication past the crimps to the atmosphere.

38 Claims, 9 Drawing Figures

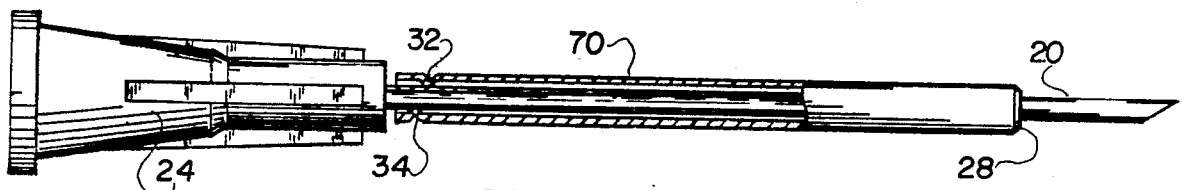
Fig. 4
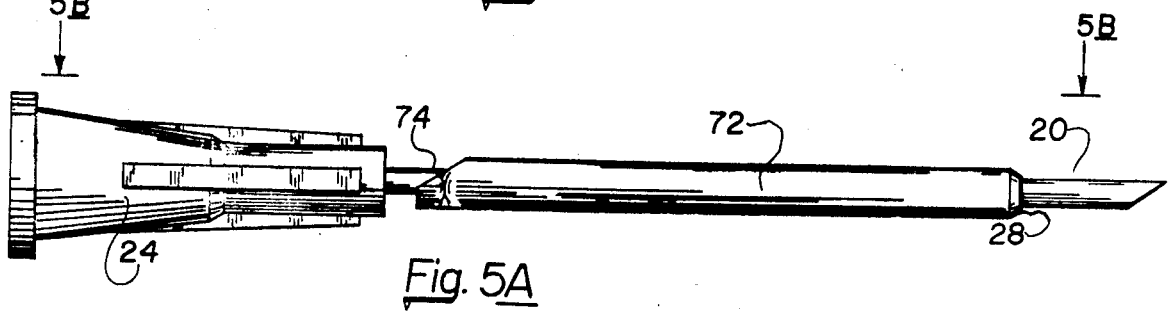
Fig. 5A
Fig. 5B
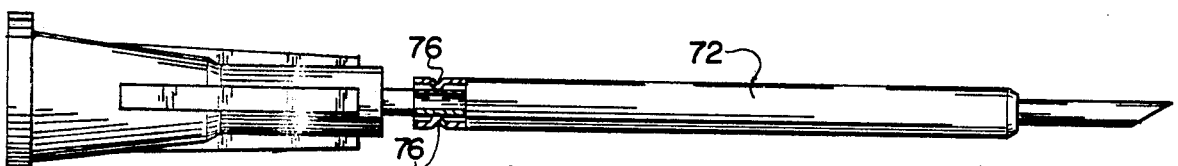
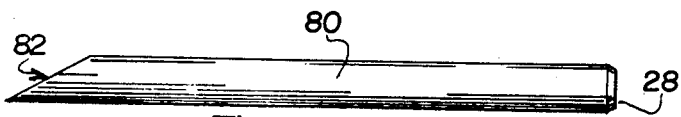
Fig. 6
Fig. 7
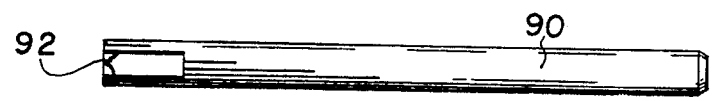
Fig. 8

SUCTION NEEDLE PROVIDING VENT CAPABILITY

CROSS-REFERENCE TO RELATED APPLICATIONS

This application provides apparatus or a device that provides venting or an air passageway from and to the interior of a vial. An allowed application entitled "SUCTION NEEDLE," filed July 17, 1985 and having Ser. No. 755,838, now U.S. Pat. No. 4,610,683 as issued Sept. 9, 1986 and is directed to a suction needle and associated apparatus. Other applications directed toward similar subject matter include application Ser. No. 509,236, as filed June 29, 1983, and entitled "VENT NEEDLE ASSEMBLY." Another application is Ser. No. 567,877, as filed Jan. 3, 1984, and entitled "NEEDLE WITH VENT FILTER ASSEMBLY." The referenced applications are filed in the name of the Applicant of this invention.

BACKGROUND OF THE INVENTION

Field of the Invention

The present invention relates to hypodermic needles used for injecting drugs into parenteral visits and/or removing the contents before or after mixing. Air venting of these vials is provided with this apparatus. Needles used with syringes are found in the general class of "SURGERY." Withdrawal of the fluid contents from vials creates negative pressure problems and this invention is directed to providing vial venting.

Venting of the stoppered vial is desirable and necessary because of the negative pressures developed as and while the fluid is withdrawn from the vial. Constant and continued venting of the vial eliminates this problem of negative pressure. Drawbacks are present in commonly-used and -known procedures. In a procedure using two needle punctures, every time a vial is punctured there is a risk of contamination. It is evident that the fewer times a container needs to be punctured, the more aseptic the interior. It is also to be noted that use of two needles in a stopper of a vial to provide venting is a very clumsy procedure as the vial must be held while securing two needles and syringe which is attached to one of the needle. This procedure requires much manipulation.

Description of the Prior Art

Heretofore, small-volume parenteral fluid containers have been pierced with hypodermic needles connected to syringes to inject fluid for reconstitution. After reconstitution the parenteral vial is repunctured and the contents removed. Alternately, a hypodermic needle-syringe combination is left within the vial while it is shaken and then the mixed drug is removed. Unfortunately, in this system the parenteral vial becomes pressurized during the procedure. As a result, a condition can and does occur, which is known as "blowback," in which particles of drug are blown into the air. This "blowback" can be very harmful to the personnel preparing such drugs. These hazards are well documented. To overcome these hazards, it is recommended that the reconstituting vial be vented at all times.

The above referenced prior application Ser. No. 755,838 is incorporated by reference to the extent applicable in this application. In this and the reference application, an additional tubular sleeve is provided so that an interior passage for air is established by the differential of diameters which are preferably about two- to six-thousandths of an inch. In this present application and the reference application, it is believed to be novel to provide the concept of a suction needle using a stainless steel needle conventionally secured to a syringe hub while providing and using a second and larger sleeve cannula as a vent conduit and securing this second sleeve or cannula with crimping means so that the sleeve tightly engages the suction needle while not altering the function or size of the needle and vent conduit.

SUMMARY OF THE INVENTION

This invention may be summarized, at least in part, with reference to its objects.

It is an object of this invention to provide, and it does provide, a needle assembly in which an air venting means is provided by and with an outer sleeve. The sharpened needle provides initial penetration of a vial stopper and is in a very close proximity to the sleeve carried by and on a syringe and provides an air vent adapted to prevent unwanted "blowback" and developed vial pressures.

It is a further object of this invention to provide, and it does provide, a penetration needle adapted to provide an air vent passageway and having a hub portion that has an air vent and may or may not include a filter. This penetration needle is of stainless steel and secured to a hub or molded member of plastic, with the socket sized and adapted to be mounted on the discharge end of a syringe. This assembly may also be used as a replacement spike so as to supply air to an administration set. This needle assembly, when used with a syringe for injection and with the outer sheath portion, is crimped in at least two places. This sleeve is not removable. The crimps as shown and described hereinafter are at least two in number and provide a positive non-slip lock of an outer sleeve to the lumen of a needle without distortion of the lumen.

The device includes a standard hypodermic (injection) needle attached to a female luer hub capable of being attached to a luer nose of a conventional syringe. A second cannula or sheath member is also of stainless steel tubing and is just a little larger than the needle. The interior spacing between the outer diameter of the needle and the interior diameter of the cannula or sheath is preferably about two- six-thousandths of an inch total. This nested-array spacing is an example of a reduced-to-practice device for a twenty-gauge needle.

In the present invention, in FIGS. 1, 2, 3 and 6, the outer tubular member is provided with an aperture formed in the side wall so that an air passageway is provided from the conducting space absent the crimps which are made in this tubular sheath to retain this sheath to the needle shank. In this application there are shown three embodiments or arrangements whereby the outer tubular member has this aperture formed in the side of this member. This aperture is forward of and toward the entering end of this member, with the crimps rearward of this aperture.

In FIGS. 4 through 8, there are depicted alternate structures of the sleeve and with the crimps used for securement. In one alternate embodiment, a straight sleeve is provided with staggered crimps. In the five remaining embodiments, the crimps may be directly opposed or may be staggered as desired. In all conditions, the suction needle is anticipated to provide venting.

In addition to the above summary, the following disclosure is detailed to insure adequacy and aid in understanding of the invention. This disclosure, however, is not intended to cover each new inventive concept no matter how it may later be disguised by variations in form or additions of further improvements. For this reason, there have been chosen specific embodiments of the suction needle as adopted for use with a vial having a resilient stopper and showing a preferred means for constructing and assembling this suction needle assembly. These specific embodiments have been chosen for the purposes of illustration and description as shown in the accompanying drawings wherein:

BRIEF DESCRIPTION OF THE DRAWINGS

FIG. 4 represents a side view, partly in section and depicting a suction needle with a metal sleeve member secured by crimps but absent a side aperture;

FIGS. 5A and 5B represent side and top views showing yet another sleeve configuration with a beveled end providing venting while the crimps are disposed in opposite array, the view 5B taken on the line 5B—5B of FIG. 5A and looking in the direction of the arrows;

FIG. 6 represents a diagrammatic side view showing of a sleeve having the exiting end as a complete bevel;

FIG. 7 represents a diagrammatic top or plan view showing yet another construction of a sleeve with an aperture formed therein, and FIG. 8 represents a diagrammatic top view with a slot formed therein.

EMBODIMENT OF FIG. 1 THROUGH FIG. 3

Figure 1:
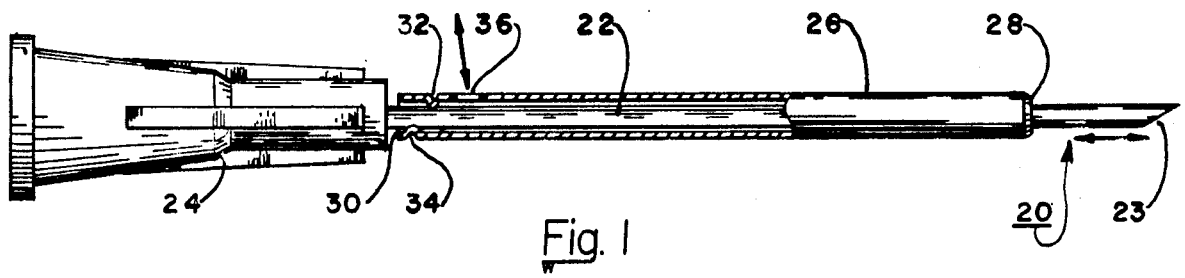
FIG. 1 represents a side view, partly in section and in a diagrammatic, enlarged scale, and showing a suction needle with a crimp means for a secured outer tubular member.

Referring next to the drawing and the suction needle illustrated therein, there is shown in enlarged scale a suction needle device designed to provide a flow of air to a stoppered vial or container. This air, as to be described hereafter, may be filtered or unfiltered. During withdrawal of the contents of the fluid in the vial or container by a syringe, air is required to prevent the interior of the vial from developing an excessive negative pressure. In FIG. 1, a conventional sharpened needle, generally identified as 20, is shown with a shaft portion 22 having a sharpened end 23. This needle is secured to a molded hub 24 which is also very conventional. To provide an air-conducting path, a stainless steel tubing portion or sleeve 26 is provided and it is contemplated that this sleeve portion be a blunt tip at one end and cut off squarely at the other end. The distal end of this sleeve toward the sharpened end of the needle is open and as the sleeve portion is larger on its inner diameter than the outer diameter of the needle shank, an air passageway is provided.

Still referring to FIG. 1, it is to be noted particularly that sleeve 26 is positioned on the shank of the needle 22 so that a distal end 28 is a short distance from the sharpened end 23 of the needle. An exit end of the sleeve 26 is identified as 30 and is a short distance from molded hub 24. This is a matter of convenience and choice as crimps 32 and 34 are made in this member 26. A transverse aperture 36 is formed in this tubular member 26. This aperture 26 is forward (rightward) of the crimps 32 and 34. It is to be noted that this aperture 36 provides an unobstructed air passage from end 28 to aperture 36. The arrows indicate air flow in and out as developed by the use of a syringe, not shown. The provision of the aperture 36 insures that air flow is not blocked if and when the crimping as in 32 and 34 produces excessive deformation in sleeve tubing 26. The needle 20 is usually of hardened steel so that any deformation that may occur with the crimping action does not appreciably change the flow capability of the syringe needle.

Figure 2:
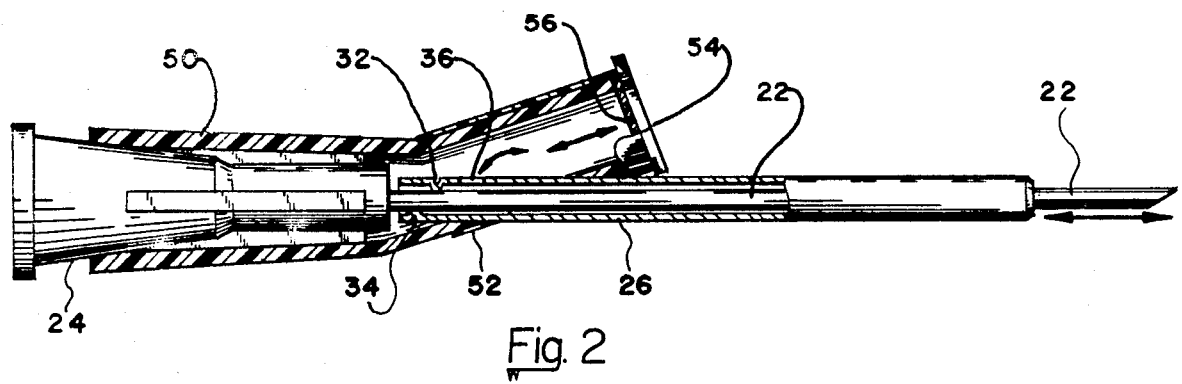
FIG. 2 represents the apparatus shown in FIG. 1, but with an additional flexible, tubular resilient member providing a filter vent.

In FIG. 2 the device of FIG. 1 is repeated, but in this embodiment the suction needle is additionally provided with a filter vent means so that exiting and entering air may be filtered. The needle and sleeve are assembled as in FIG. 1 and an added tubular member is also utilized. This resilient tubular member is identified as 50 and has one wall portion punctured at 52. The left end of member 50 is stretched sufficiently to grip the hub 24. The other end of tubular member 50 has an inserted or attached closure cap 54. A filter portion 56 may be provided with the closure member 54 so as to exclude any bacteria present in the atmosphere. Whether the closure 54 is positioned in or outside of the tube is merely a matter of preference, and no patentable distinction is ascribed thereto.

Figure 3:
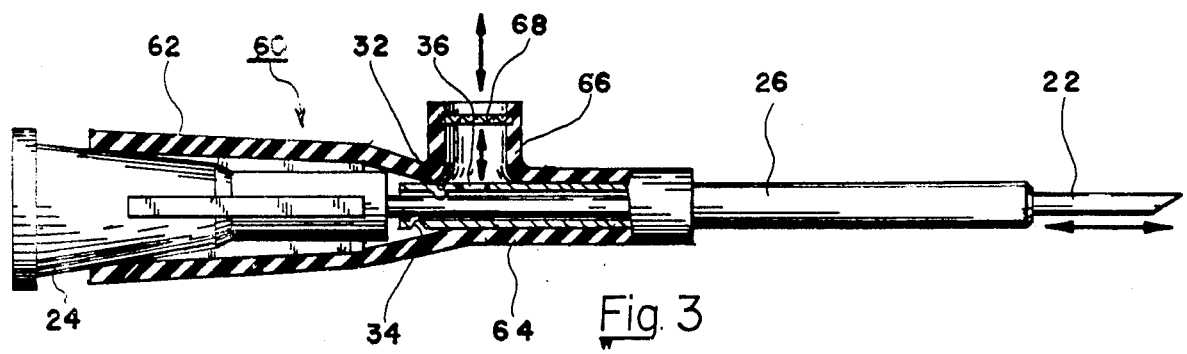
FIG. 3 represents the apparatus as shown in FIG. 2, but with the filter vent arranged at substantially right angles to the shank of the needle.

In FIG. 3 the device of FIG. 1 is also utilized, but rather than with a tubular member as in FIG. 2 this filter device employs a molded member identified as 60. The leftward portion, identified as 62, is sized so as to be a stretch fit for the hub 24. Rightward of portion 62 is a reduced tubular portion 64 which is adapted to snugly fit the outside of tubular sleeve 26. A transverse portion 66 is provided in this molding and is closed by a filter disc 68. The member 60 is contemplated to be made of resilient material and sized for ready mounting on the device of FIG. 1.

The aperture 36 in FIGS. 1, 2 and 3 is utilized to directly communicate with the atmosphere. This aperture 36 indirectly communicates with atmosphere or through a filter device 56 as provided in FIG. 2, and 68 in FIG. 3. The crimping includes at least two crimps in staggered array so that air passes by these crimps. In later described embodiments, the crimps may be opposite one another. The crimps are not sufficiently deep to distort the inner cannula of the needle. As in the reference application, this suction needle size is selected as to size and length to accommodate the intended use.

The devices of FIGS. 1, 2 and 3 are contemplated to be very low in cost and provide a one-time use. Inexpensive cost is desired so as to reduce the expenses particularly incurred in and with treatments using potent drugs. This device, whether the embodiment of FIGS. 1, 2 or 3, may provide filtered venting of a vial. The crimping of the sleeve 26 to the shank 22 is with only very localized indenting and limited deformation so as not to impair the needle lumen's fluid flow characteristics while providing a secure lock of the sleeve to the needle. The needle point 23 penetrates the resilient stopper of the vial followed by the sleeve 26. Because of potential coring of the stopper vial, needle sizes for this suction needle device are kept small and generally are a maximum of eighteen gauge. The sleeve is conventionally of stainless steel with a wall thickness of four- to ten-thousandths of an inch. This arrangement allows for air passage in the annular space which is sufficient for venting the vial. The use of this suction needle is usually with antineoplastic drugs with which the attendant should not come in contact.

The crimps 32 and 34 are contemplated to be tapered or knife-like indents. Crimp securing, as shown in KINNE, U.S. Pat. No. 3,527,025, wherein the wire is bent from a straight line, is not anticipated or desired. Each crimp is very localized and deforms the sleeve 26 and, as shown, is not intended to distort the internal passage in the needle 26. The aperture 36 inside of sleeve 26 is easily provided in the side of sleeve 26. Crimping to the rest of this aperture therewith permit greater air flow since the passageway from end 28 to the aperture 36 is not distorted. The crimps produced in this device are not so critical as to their depth, other than precluding distortion of the inner needle lumen. The crimps are anticipated to be only two in number and may be staggered. This does not preclude more crimps and does not preclude a plurality of crimps along or substantially along the same side.

The filter means in FIGS. 2 and 3 is anticipated to exclude unwanted air-carried bacteria and, if any fluid from the vial contents accidentally is brought to the filter, this filter provides a fluid barrier. The filter membrane is anticipated to be sufficiently supported so as not to tear in use or be distorted from its intended use.

EMBODIMENT OF FIG. 4

The representation in FIG. 4 is of a suction needle in which the sleeve 70 is a substantially square cut-off length of tubing. The front or forward end is beveled at 28 to provide ease of penetration of a stoppered vial. The bevel 28 is as described for FIG. 1. Staggered crimps 32 and 34 are made in sleeve 70 as described in connection with FIG. 1. Air may flow in the passageway between the shank of needle 20 and the inner diameter of sleeve 70. The crimps 32 and 34, although providing securement of the sleeve 70 on the needle shank, are not so deep as to cut off air flow in the air passage and, as shown, the exiting end of the sleeve 70 is a short distance from the hub 24 which retains the needle.

EMBODIMENT OF FIGS. 5 A AND 5 B

In FIGS. 5 A and 5 B, there is depicted an alternate construction of the sleeve and crimps. As shown, since 72 is beveled at its entering end 28, as described above. The rear or exiting end of sleeve 72 is cut with a small slope portion, identified as 74. As seen in FIG. 5 B, two like crimps 76 are made in sleeve 72 and are positioned directly opposite or substantially opposite each other, and at or slightly to the rear of the forward end of slope 74. This anticipates providing an air flow or communication passage from the front of the sleeve 72 to this sloped portion. The crimps 76 are not anticipated to change the flow capability of the needle. More than two crimps 76 may be provided, but at least two are desired.

EMBODIMENT OF FIG. 6

In FIG. 6, the sleeve of FIGS. 5 A and 5 B is suggested but, rather than a sloped cut leaving a portion of transverse cut end, the sleeve (identified as 80) is more fully cut at a slope identified as 82. The bevel 28 is made and, as in FIGS. 5 A and 5 B, the crimps are made in sleeve 80 to secure said sleeve to the shank of a needle, not depicted.

EMBODIMENT OF FIG. 7

In FIG. 7, sleeve 86 is beveled at the forward end 28, as above. Rather than sloped cut-off of the rear portion of a sleeve, there is shown a rectangular cut-out aperture, identified as 88. This sleeve 86 is crimped so the cut-off aperture 88 is not distorted by the crimping action.

EMBODIMENT OF FIG. 8

Referring next, and finally, to the drawings, there is shown in FIG. 8 a sleeve 90 which is substantially like that in FIG. 7 but, rather than an aperture, there is formed a slot, identified as 92. Crimping is as above. Slot 92 is anticipated to be open to the atmosphere so that communication to the interior passageway between needle and sleeve is insured.

The showings of FIGS. 4, 5 A, 5 B, 6, 7 and 8 are illustraembodiments that are contemplated to provide positive communication of the passageway between needle shank and sleeve while insuring that a crimping action does fixedly secure the sleeve to the needle shank. Crimps are anticipated to be by automatic, high-speed operation, and small tolerances are anticipated. Usually, the crimps are staggered, but substantially opposite positioning or side-by-side crimps may be utilized. The essence of this invention is to provide a flow path for air to and from the atmosphere while the lumen of the needle is not appreciably changed or diminished.

What is believed to be novel is the inexpensive suction needle of this invention and the discovery that the tubular sleeve may be secured to the shaft of the needle by simply making two or more crimps without appreciably distorting the lumen as to flow capacity.

The needle used with this device is used for removing drugs from a container. This needle is not contemplated to be used with a patient and the skin of this patient is not to be penetrated with this needle because of the attached sleeve. The needle shank 22 is preferably sharpened at 23 to decrease the effort or force needed to pass through the housing or the stopper to be penetrated. The sleeve 26, 70, 72, 80, 82 or 90 is usually of a thin wall to reduce the effort of passing through the stopper. The sleeve is conventionally cut off at its front end, substantially normal to its axis, and beveled, but other cut-off configurations may be provided, including a squared edge. For economical reasons, the members 50 or 60 are of a partially resilient material such as polyurethane, plastic or rubber.

The construction and use of the above-shown and -described suction needle device provides a basis for a method of constructing and using such a device. This method includes the steps of:

atttaching a hollow metal needle shank to one end of the hub and sharpening said needle at a distal entering other end, said needle and hub providing a fluid conduit therethrough;

positioning and securing a thin-walled tubular sleeve of a lesser length than the shank of the needle, said sleeve having an internal diameter larger than the outer diameter of the needle, with said tubular sleeve having an entering and a rear end and coaxially aligned with the shank of the needle when mounted and secured thereto, providing a substantially annular space therebetween, with said space providing an air conduit between the shank of the needle and sleeve;

forming an aperture in and through the side wall of the thin-walled tubular sleeve and positioning said aperture near that end of the tubular sleeve near the hub, or alternately providing an air access inlet and outlet at the rear end of the sleeve as by an angled slope outlet, slot, or an opening to the atmosphere;

forming at least two localized crimps in said tubular sleeve, these crimps oppositely, longitudinally or staggered in displacement, and providing securing of the sleeve to the needle shank to prevent movement therealong, said crimps sufficient to locally deform the sleeve without substantially deforming the lumen of the needle, and disposing said crimps between said formed aperture and that end of the tubular sleeve adjacent the attached hub of the needle, or said crimps formed in the sleeve, with the air passage open to the rear end of the sleeve or to an air exit at a sloped cut-off, a slot or aperture to the rear of the crimps.

It is to be noted that the above application anticipates a high-speed automatic production of the device. Accordingly, the crimping to establish and limit penetration is performed by automatic apparatus with control stop means, which steps or limitators may be adjustable. The filter means provided in FIG. 2 may be with a molded sleeve that is sized and adapted to be inserted into the end of the tubular member 50 as a friction fit or may have adhesive used therewith. It is also contemplated that the sleeve portion that retains the filter 56 may be secured to the resilient tube 50 by adhesive or sonic welding as determined by the production techniques.

The resilient retainer 60 of FIG. 3 anticipates a substantially transverse or right-angle extension 66 into which a rigid filter disc 68 is mounted, using the resilient of member 60. This is not to preclude securing the filter 68 by adhesive with or without a tubular support. The production line and available manufacturing procedures are determinative of the process utilized. Conventionally, the filter is adapted to be a barrier to the passage of bacteria, but the invention is not limited thereto since, as in FIG. 1, the aperture 36 is open to atmosphere. Conventionally, the filter 68 is formed as disc-like, but this is only a matter of preference as other configurations may be provided. This filter 68 may also be a plug cap or the like, and the filter structure is merely a matter of preference. The securing of the filter 68 in the molding 60 (FIG. 3) may include a cap member or sleeve 54, as in FIG. 2, and may be an inserted molding or may be an outer positioned cap and adhesive. Other securing devices are shown in the reference application. The alternate structures shown in FIGS. 4 through 8 anticipate no filtering of the inflow and outflow of air. These embodiments are particularly disposed to bring the interior of the vial to equalized pressure during withdrawal or addition of fluid from the vial.

Terms such as "left," "right," "up," "down," "bottom," "top," "front," "back," "in," "out" and the like are applicable to the three embodiments shown and described in conjunction with the drawings. These terms are merely for the purpose of description and do not necessarily apply to the position in which the suction needle device may be constructed or used.

While particular embodiments of this device have been shown and described, it is to be understood that the invention is not limited thereto and protection is sought to the broadest extent the prior art allows.

What is claimed is:

1. A suction needle device for fluid withdrawal and venting the interior of a stoppered vial or container, said device including:
    (a) a hollow metal needle having a shank attached at one end to a hub, said needle having a sharpened outer end and through said hub providing a fluid conduit through said needle;
    (b) a thin-walled tubular sleeve of a lesser length than the shank of the needle and having an internal diameter larger than the outer diameter of the needle, said tubular sleeve having an entering and a rear end and coaxially aligned with the shank of the needle when mounted and secured thereto, providing a substantially annular space therebetween, with said space providing an air conduit between the shank of the needle and sleeve;
    (c) an aperture formed in and through the side wall of the thin-walled tubular sleeve and near that end of the tubular sleeve near the hub, and
    (d) at least two localized crimps formed in said tubular sleeve, these crimps longitudinally displaced and providing securing of the sleeve to the needle shank to prevent movement therealong, said crimps sufficient to locally deform the sleeve without substantially deforming the lumen of the needle, these crimps disposed between said formed aperture and that end of the tubular sleeve adjacent the attached hub of the needle.

2. A suction needle device as in claim 1 in which the needle has its sharpened end and the entering end of the tubular sleeve arranged for ease in penetration of a resilient stopper of a vial.

3. A suction needle device as in claim 1 in which the crimps are V-shaped and the longitudinal displacement and penetration is rearward from the aperture formed in the thin-walled tubular sleeve, with side crimps established by mechanical means.

4. A suction/needle device as in claim 1 in which there are at least two crimps formed in the outer tubular sleeve and with at least one crimp disposed on opposite sides of the shank of the needle.

5. A suction needle device as in claim 1 in which the thin-walled tubular member has a wall thickness of five-thousandths of an inch or less and the entering end of said tubular member is chamfered to provide a diminished effort for penetration of a resilient stopper.

6. A suction needle device as in claim 1 in which the rear end of the thin-walled tubing is proximate the forward end of the hub which is secured to the needle.

7. A suction needle device as in claim 1 which further includes a resilient tubular member which is cut to a determined length, with a first and second end, and with the first end stretched sufficiently to snugly engage and be seated upon the needle hub and with the needle and secured thin-walled tubular sleeve passed through a penetrated intermediate side wall portion of the resilient tubular member and with the needle and secured thin-walled tubular sleeve extending beyond this tubular resilient member, and with this second end of the resilient tubular member closed with a filter vent cap, the aperture in the tubular sleeve in flow communication with the interior of the resilient tubular member.

8. A suction needle device as in claim 7 in which the closing of the second end of the resilient tubular member is with a filter carried in a cap member that is retained with and by a tubular sleeve that is a friction fit within the tubular member.

9. A suction needle device as in claim 7 in which the filter in the vent cap is adapted to exclude the passage therethrough of bacteria.

10. A suction needle device as in claim 1 which further includes a resilient tubular outer member formed as a molding which includes a short transverse or substantially right-angle outward extension which is intermediate first and second ends of the molded outer member and with the first end sized to snugly engage the needle hub when said molding is stretched and said second end is sized to snugly engage and be seated on the secured thin-walled tubular sleeve, this intermediate extension having an open end that is closed by a retained filter member; this intermediate extension is in flow communication with the interior of the resilient molded member and the aperture in the thin-walled tubular sleeve.

11. A suction needle device as in claim 10 in which the filter is a disc-like member and the filter is adapted to exclude the passage therethrough of bacteria.

12. A suction needle device as in claim 11 in which the filter member is carried in a cap member that is retained in the extension and by a friction fit.

13. A suction needle device as in claim 12 in which there are at least two crimps formed in the outer tubular sleeve and with at least one crimp disposed on opposite sides of the shank of the needle.

14. A suction needle device for fluid withdrawal and venting the interior of a stoppered vial or container, said device including:
(a) a hollow metal needle having a shank attached at one end to a hub, said needle having a sharpened other end and through said hub providing a fluid conduit through said needle;
(b) a thin-walled tubular sleeve of a lesser length than the shank of the needle and having an internal diameter larger than the outer diameter of the needle, said tubular sleeve having an entering and a rear end and coaxially aligned with the shank of the needle when mounted and secured thereto, providing a substantially annular space therebetween, with said space providing an air conduit between the shank of the needle and sleeve, and
(c) at least two localized crimps formed in said tubular sleeve, these crimps providing securing of the sleeve to the needle shank to prevent movement therealong, said crimps sufficient to locally deform the sleeve without substantially deforming the lumen of the needle, these crimps disposed at that end of the tubular sleeve adjacent the attached hub of the needle.

15. A suction needle device as in claim 14 in which the needle has its sharpened end and the entering end of the tubular sleeve chamfered for ease in penetration of a resilient stopper of a vial.

16. A suction needle device as in claim 14 in which the crimps are staggered and are disposed on opposite sides of the needle shank.

17. A suction needle device as in claim 14 in which the crimps are substantially opposite or are opposite each other along the needle shank.

18. A suction needle device as in claim 17 in which the rear end of the sleeve is formed at an angle such that the opening is oblique and provides an air passage connection with said annular space between the needle and sleeve.

19. A suction needle device as in claim 17 in which the sleeve is formed with an aperture in the side of the sleeve, and with this aperture at least partly open and in communication with said annular space between the needle and sleeve.

20. A suction needle device as in claim 17 in which there is formed a slot extending from the rear end and inward to a determined distance ahead of the crimps, said slot in communication with said annular space between the needle and sleeve.

21. A method of constructing and using a suction needle device for fluid withdrawal and venting of a stoppered vial or container, said method including the steps of:
(a) attaching a hollow metal needle shank to one end of a hub and sharpening said needle at a distal entering other end, said needle and hub providing a fluid conduit therethrough;
(b) positioning a thin-walled tubular sleeve of a lesser length than the shank of the needle, said sleeve having an internal diameter larger than the outer diameter of the needle, with said tubular sleeve having an entering and a rear end and coaxially aligning said sleeve with the shank of the needle when mounted and providing a substantially annular space therebetween, said space providing an air conduit between the shank of the needle and sleeve;
(c) forming an aperture in and through the side wall of the thin-walled tubular sleeve and positioning said aperture near that end of the tubular sleeve near the hub, and
(d) forming at least two localized crimps in said tubular sleeve, these crimps longitudinally displaced and providing a securing of the sleeve to the needle shank to prevent movement therealong, said crimps sufficient to locally deform the sleeve without substantially deforming the lumen of the needle, these crimps disposed between said formed aperture and that end of the tubular sleeve adjacent the attached hub of the needle.

22. A method of constructing and using a suction needle device as in claim 21 which includes positioning the sharpened needle and shaping the entering end of the tubular sleeve so as to provide a combination of members with an ease in penetration of a resilient stoppered vial.

23. A method of constructing and using a suction needle device as in claim 21 which includes forming V shaped crimps with a crimping tool and positioning said crimps with a longitudinal displacement and penetration which is rearward from the aperture formed in the thin-walled tubular sleeve, with the depth of said crimps established by mechanical means.

24. A method of constructing and using a suction needle device as in claim 21 which includes providing at least two crimps in the outer tubular sleeve and disposing at least one crimp on opposite sides of the shank of the needle.

25. A method of constructing and using a suction needle device as in claim 21 in which the thin-walled tubular sleeve is selected with a wall thickness of five-thousandths of an inch or less and the entering end is chamfered to provide means for a diminshed effort for penetration of a resilient stopper.

26. A method of constructing and using a suction needle device as in claim 21 which further includes the steps of securing an added resilient tubular member and cutting this tubular member to a determined length with a first and second end, and stretching said first end sufficiently to snugly engage and seat upon the needle hub and passing the needle and secured thin-walled tubular sleeve through a penetrated intermediate side wall portion of the resilient tubular sleeve, with said needle and secured thin-walled tubular sleeve extending beyond this resilient tubular member, and closing this second end of the resilient tubular member with a filter vent cap, this resilient tubular member positioned so that the aperture in the tubular sleeve in in flow communication with the interior of the resilient tubular member.

27. A method of constructing and using a suction needle device as in claim 26 in which the closing of the second end of the added resilient tubular member is with a filter carried in a cap member and includes retaining said filter by a tubular sleeve that is a friction fit within the tubular member.

28. A method of constructing and using a suction needle device as in claim 26 which includes forming the filter from a material that is adapted to exclude the passage therethrough of bacteria.

29. A method of constructing and using a suction needle device as in claim 21 which further includes the steps of securing an added resilient tubular member which is formed as a molding which includes a short transverse or substantially right angle outwardly-extending tubular extension which is intermediate a first and second end of said molded resilient tubular member and stretching said first end so as to snugly engage the needle hub and stretching the second end of the molding so as to snugly engage the exterior of the secured thin-walled tubular sleeve, and positioning this intermediate outward tubular extension so as to be in flow communication with the interior of the molded resilient member and the aperture in the thin-walled tubular member.

30. A method of constructing and using a suction needle device as in claim 29 which includes forming the filter from a material that is adapted to exclude the passage therethrough of bacteria.

31. A method of constructing and using a suction needle device as in claim 30 which further includes retaining this filter member in a cap and retaining this cap in the tubular extension by a friction fit.

32. A method of constructing and using a suction needle device as in claim 30 which includes providing at least two crimps in the outer tubular sleeve and disposing at least one crimp on opposite sides of the shank of the needle.

33. A method of constructing and using a suction needle device for fluid withdrawal and venting of a stoppered vial or container, said method including the steps of:
(a) attaching a hollow metal needle shank to one end of a hub and sharpening said needle at a distal entering other end, said needle and hub providing a fluid conduit therethrough;
(b) positioning a thin-walled tubular sleeve of a lesser length than the shank of the needle, said sleeve having an internal diameter larger than the outer diameter of the needle, with said tubular sleeve having an entering and a rear end and coaxially aligned with the shank of the needle when mounted and providing a substantially annular space therebetween, with said space providing an air conduit between the shank of the needle and sleeve, and
(c) forming at least two localized crimps in said tubular sleeve, these crimps providing securing of the sleeve to the needle shank to prevent movement therealong, said crimps sufficient to locally deform the sleeve without substantially deforming the lumen of the needle, these crimps disposed near that end of the tubular sleeve adjacent the attached hub of the needle.

34. A method of constructing and using a suction needle device as in claim 33 which further includes positioning the crimps in a staggered array and disposing said crimps on opposite sides of the needle shank.

35. A method of constructing and using a suction needle device as in claim 33 which further includes disposing and positioning the crimps substantially opposite or opposite each other along the needle shank.

36. A method of constructing and using a suction needle device as in claim 35 which further includes forming the rear of the sleeve with a sloped configuration, and providing in and with this slope an air passage to said annular space between the needle and sleeve.

37. A method of constructing and using a suction needle device for fluid withdrawal and venting of a stoppered vial or container, said method including the steps of:
(a) attaching a hollow metal needle shank to one end of a hub and sharpening said needle at a distal entering other end, said needle and hub providing a fluid conduit therethrough;
(b) positioning a thin-walled tubular sleeve of a lesser length than the shank of the needle, said sleeve having an internal diameter larger than the outer diameter of the needle, with said tubular sleeve having an entering and a rear end, and coaxially aligning said sleeve with the shank of the needle when mounted and providing a substantially annular space therebetween, said space providing an air conduit between the shank of the needle and sleeve;
(c) forming an aperture in the side wall of the sleeve, and positioning said aperture in the rear of the sleeve so that at least a portion of this aperture is in flow communication with said annular space between the needle and sleeve, and
(d) forming at least two localized crimps in said tubular sleeve, these crimps longitudinally displaced and providing a securing of the sleeve to the needle shank to prevent movement therealong, said crimps sufficient to locally deform the sleeve without substantially deforming the lumen of the needle, these crimps disposed between said formed aperture and that end of the tubular sleeve adjacent the attached hub of the needle.

38. A method of constructing and using a suction needle device for fluid withdrawal and venting of a stoppered vial or container, said method including the steps of:
(a) attaching a hollow metal needle shank to one end of a hub and sharpening said needle at a distal entering other end, said needle and hub providing a fluid conduit therethrough;
(b) positioning a thin-walled tubular sleeve of a lesser length than the shank of the needle, said sleeve having an internal diameter larger than the outer diameter of the needle, with said tubular sleeve having an entering and a rear end, and coaxially aligning said sleeve with the shank of the needle when mounted and providing a substantially annular space therebetween, said space providing an air conduit between the shank of the needle and sleeve;

(c) forming a slot in and through the side wall of the thin-walled tubular sleeve and positioning said slot to the rear and so as to be in communication with the annular space between the needle and sleeve, and (d) forming at least two localized crimps in said tubular sleeve, these crimps longitudinally displaced and providing a securing of the sleeve to the needle shank to prevent movement therealong, said crimps sufficient to locally deform the sleeve without substantially deforming the lumen of the needle, these crimps disposed between said formed aperture and that end of the tubular sleeve adjacent the attached hub of the needle.

* * * * *